United States Patent
Hayashi et al.

(10) Patent No.: US 10,739,474 B2
(45) Date of Patent: Aug. 11, 2020

(54) SCINTILLATOR ARRAY, METHOD OF MANUFACTURING SCINTILLATOR ARRAY, RADIATION DETECTOR, AND RADIATION INSPECTION DEVICE

(71) Applicants: KABUSHIKI KAISHA TOSHIBA, Tokyo (JP); TOSHIBA MATERIALS CO., LTD., Yokohama-Shi (JP)

(72) Inventors: Makoto Hayashi, Chigasaki (JP); Hiroyasu Kondo, Yokohama (JP); Hiroshi Ichikawa, Miura (JP); Yoshitaka Adachi, Yokohama (JP); Yukihiro Fukuta, Yokohama (JP)

(73) Assignees: Kabushiki Kaisha Toshiba, Minato-Ku (JP); Toshiba Materials Co., Ltd., Yokohama-Shi (JP)

(*) Notice: Subject to any disclaimer, the term of this patent is extended or adjusted under 35 U.S.C. 154(b) by 0 days.

(21) Appl. No.: 16/429,367

(22) Filed: Jun. 3, 2019

(65) Prior Publication Data
US 2019/0302284 A1    Oct. 3, 2019

Related U.S. Application Data

(63) Continuation of application No. PCT/JP2017/043646, filed on Dec. 5, 2017.

(30) Foreign Application Priority Data

Dec. 6, 2016  (JP) .................................. 2016-236921

(51) Int. Cl.
*G01T 1/20*    (2006.01)
*G01T 1/202*   (2006.01)
(Continued)

(52) U.S. Cl.
CPC .............. *G01T 1/2018* (2013.01); *A61B 6/03* (2013.01); *G01T 1/20* (2013.01); *G01T 1/2002* (2013.01); *G01T 1/2023* (2013.01); *G21K 4/00* (2013.01)

(58) Field of Classification Search
CPC .... C04B 2235/3224; C04B 2235/5436; C04B 2235/446; G01T 1/2023
See application file for complete search history.

(56) References Cited

U.S. PATENT DOCUMENTS 4,733,088 A      3/1988  Yamada et al.
6,504,156 B1 *   1/2003  Takahara ........... C09K 11/7771
                                                250/361 R
(Continued)

FOREIGN PATENT DOCUMENTS

JP    H05-016756 B2    3/1993
JP       5241979 B2    7/2013
(Continued)

OTHER PUBLICATIONS

International Search Report and Written Opinion (Application No. PCT/JP2017/043646) dated Feb. 6, 2018.

*Primary Examiner* — Kenneth J Malkowski
(74) *Attorney, Agent, or Firm* — Burr & Brown, PLLC

(57) ABSTRACT

A scintillator array includes a first scintillator element, a second scintillator element, and a reflector provided between the first and second scintillator elements and having a width of 80 μm or less therebetween. Each scintillator element includes a polycrystal containing a rare earth oxysulfide phosphor, the polycrystal having a radiation incident surface of 1 mm or less×1 mm or less in area. An average crystal grain diameter of the polycrystal is not less than 5 μm nor more than 30 μm, the average crystal grain diameter being defined by an average intercept length of crystal grains in an observation image of the polycrystal with a scanning elec- (Continued)

tron microscope. A maximum length or a maximum diameter of defects on the polycrystal is 40 μm or less.

6 Claims, 4 Drawing Sheets

(51) Int. Cl.
*A61B 6/03* (2006.01)
*G21K 4/00* (2006.01)

(56) References Cited

U.S. PATENT DOCUMENTS

| | | |
|---|---|---|
| 2006/0065842 A1 | 3/2006 | Okamura et al. |
| 2006/0145085 A1* | 7/2006 | Fukuta ................ C04B 35/547 250/370.11 |
| 2012/0145962 A1* | 6/2012 | Fukuta ............... C09K 11/7774 252/301.4 R |
| 2013/0108008 A1* | 5/2013 | Levene ................ G01T 1/2002 378/4 |
| 2014/0301527 A1* | 10/2014 | Morimoto ............ G01N 23/046 378/4 |
| 2017/0199285 A1 | 7/2017 | Adachi et al. |

FOREIGN PATENT DOCUMENTS

| | | |
|---|---|---|
| WO | 2004/077098 A1 | 9/2004 |
| WO | 2016/047139 A1 | 3/2016 |

\* cited by examiner

SCINTILLATOR ARRAY, METHOD OF MANUFACTURING SCINTILLATOR ARRAY, RADIATION DETECTOR, AND RADIATION INSPECTION DEVICE

CROSS-REFERENCE TO RELATED APPLICATIONS

This application is a continuation of prior International Application No. PCT/JP2017/043646 filed on Dec. 5, 2017; the entire contents of all of which are incorporated herein by reference.

BACKGROUND OF THE INVENTION

1. Field of the Invention

Embodiments described herein generally relate to a scintillator array, a method of manufacturing the scintillator array, a radiation detector, and a radiation inspection device.

2. Description of Related Art

Inspections such as medical diagnosis and industrial non-destructive inspection can use a radiation inspection device such as an X-ray tomograph (hereinafter, described as an X-ray CT (Computed Tomography) scanner). The X-ray CT scanner includes an X-ray tube (X-ray source) which performs irradiation with fan-shaped fan beam X-rays and an X-ray detector having a plurality of X-ray detection elements, and the above-described X-ray tube and the above-described X-ray detection elements are arranged through an inspection object therebetween. The X-ray CT scanner performs the irradiation with the fan beam X-rays from the X-ray tube while rotating the X-ray tube with respect to the inspection object, and the X-ray detector collects X-ray absorption data formed based on X-rays which the inspection object transmits. Subsequently, a computer analyzes the data to reproduce a tomogram.

The X-ray detector widely use a detection element having a solid scintillator. In the X-ray detector using the solid scintillator, it is too easy to increase the number of channels by downsizing the detection element, thus making it possible to further increase the resolution of the X-ray CT scanner.

The solid scintillator is composed of, for example, a ceramic scintillator material. Among the above ceramics scintillator materials, a rare earth oxysulfide-based phosphor ceramics (rare earth oxysulfide phosphor) is high in light emission efficiency and has characteristics suitable for a scintillator. For this reason, an X-ray detector which includes the detection elements including the solid scintillator composed of the rare earth oxysulfide-based phosphor ceramics and photodiodes is becoming widely used.

There have been conventionally made various proposals regarding transparency, sinterability, and the like of the solid scintillator composed of the above-described rare earth oxysulfide phosphor. An X-ray CT scanner in recent years is required for downsizing of the detection element, or the like with an increase in the number of channels for the purpose of an increase in resolution. Moreover, for photographing of a fine structure, a detector whose size per element of the detection element is ½ or less smaller than the conventional one is under development.

Moreover, an increase in resolution and an increase in fineness of the X-ray CT scanner lead to an artifact of generated images when the computer analyzes the X-ray absorption data in accordance with the X-rays through the inspection object to reproduce a tomogram. The artifact occurs due to non-uniformity of local sensitivity of a scintillator array, or the like. Because the occurrence of the artifact is obstacles of medical diagnosis and non-destructive inspection, it is desired that a sensitivity distribution of the scintillator array is made more uniform.

SUMMARY OF THE INVENTION

Figure 1:
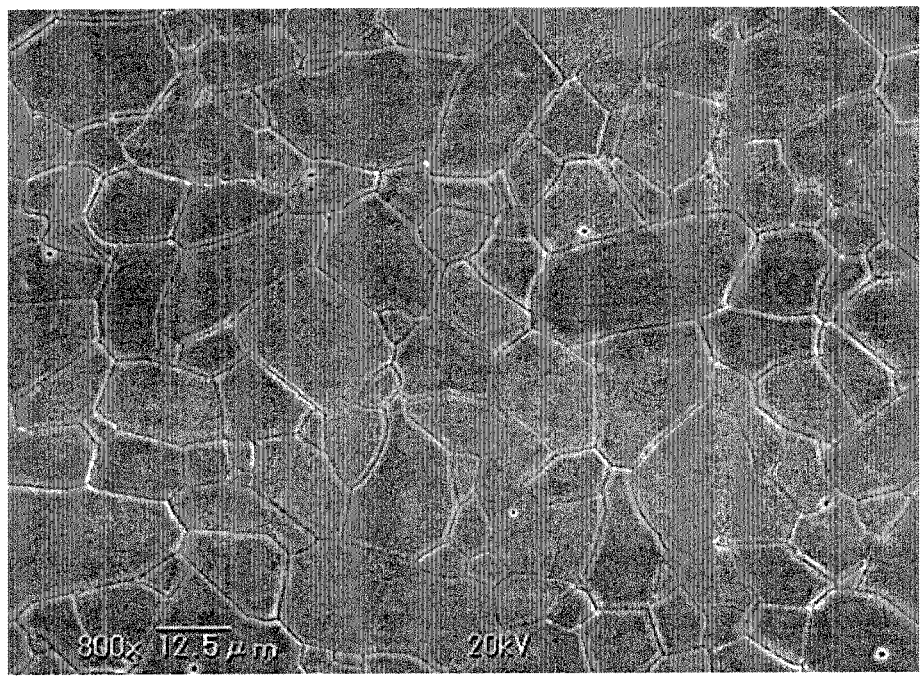
FIG. 1 is a view illustrating a crystal grain structure of a sintered compact of a solid scintillator.

A scintillator array of an embodiment includes: A scintillator array comprising: a first scintillator element; a second scintillator element; and a reflector provided between the first and second scintillator elements and having a width of 80 μm or less therebetween. Each scintillator element includes a polycrystal containing a rare earth oxysulfide phosphor, the polycrystal having a radiation incident surface of 1 mm or less×1 mm or less in area.

An average crystal grain diameter of the polycrystal is not less than 5 μm nor more than 30 μm, the average crystal grain diameter being defined by an average intercept length of crystal grains in an observation image of the polycrystal with a scanning electron microscope. A maximum length or a maximum diameter of defects on the polycrystal is 40 μm or less.

Hereinafter, an embodiment for carrying out the present invention will be explained with reference to the drawings. The drawings are schematic, and for example, sizes such as a thickness and a width of each of components are sometimes different from actual sizes of the component. Further, in the embodiment, substantially the same components are denoted by the same reference signs, and the explanation is sometimes omitted.

A scintillator array of the embodiment converts a radiation ray such as an X-ray to visible light or the like. The scintillator array includes a plurality of scintillator elements, and a reflector disposed between the scintillator elements, which reflects a radiation ray. The plurality of scintillator elements are each formed by cutting a sintered compact (polycrystal) of a solid scintillator composed of a ceramic scintillator material. Accordingly, the plurality of scintillator elements each have the above-described polycrystal.

The solid scintillator is produced by molding a rare earth oxysulfide phosphor powder in a suitable shape and sintering this powder. A rectangular bar-shaped or flat plate-shaped scintillator plate formed by cutting a sintered compact of the produced solid scintillator is sliced to be processed into a plurality of rectangular parallelepiped scintillator elements. A detection element using the solid scintillator is constituted by a scintillator array formed by integrating the above-described plurality of scintillator elements with reflective layers (reflectors) each having a width (a width between the scintillator elements) of about 80 μm each interposed therebetween, for example.

The ceramic scintillator material is composed of, for example, a sintered compact (polycrystal) of a rare earth oxysulfide phosphor containing praseodymium (Pr) as an activator. The above-described rare earth oxysulfide phosphor includes an oxysulfide of at least one rare earth element selected from the group consisting of yttrium (Y), gadolinium (Gd), lanthanum (La), and lutetium (Lu).

The rare earth oxysulfide phosphor preferably has a composition substantially expressed by

a formula: $A_2O_2S{:}Pr$      (1)

(in the formula, A represents at least one rare earth element selected from the group consisting of Y, Gd, La and Lu).

Among the rare earth elements, gadolinium (Gd) has a large X-ray absorption coefficient and contributes to an improvement in light output by the ceramic scintillator material composed of the above-described rare earth oxysulfide phosphor. Accordingly, it is more preferable to use a sintered compact of a rare earth oxysulfide phosphor expressed by a formula: $Gd_2O_2S{:}Pr$ as the ceramic scintillator material. Note that another rare earth element may substitute for a part of gadolinium (Gd). A substitution amount according to another rare earth element is preferably set to 10 mol % or less of all the rare earth elements.

The ceramic scintillator material (the above-described rare earth oxysulfide phosphor) more preferably has a composition substantially expressed by

a formula: $(Gd_{1-x}A'_x)_2O_2S{:}Pr$      (2)

(in the formula, A' represents at least one element selected from the group consisting of Y, La, and Lu, and x is a number satisfying $0 \leq x \leq 0.1$).

Praseodymium (Pr) to be used as the activator that increases light output of the rare earth oxysulfide phosphor can reduce afterglow as compared with other activators. Accordingly, the rare earth oxysulfide phosphor containing Pr as the activator is effective as a fluorescence generator of an X-ray detector.

The content of Pr is preferably not less than 0.001 mol % nor more than 10 mol % relative to a phosphor host (for example, $Gd_2O_2S$). The content of Pr exceeding 10 mol % causes a decrease in light output. On the other hand, the content of Pr being less than 0.001 mol % fails to provide a sufficient effect as a main activator. The content of Pr is more preferably not less than 0.01 mol % nor more than 1 mol %.

The rare earth oxysulfide phosphor may contain a small amount of at least one element selected from the group consisting of Ce (cerium), Zr (zirconium) and P (phosphorus) as a coactivator in addition to Pr as the main activator. The addition of these elements has effect to suppression of exposure deterioration, suppression of afterglow, and so on. A total amount of the contents of these coactivators is preferably not less than 0.00001 mol % nor more than 0.1 mol % relative to the phosphor host.

A purity of the rare earth oxysulfide phosphor is preferably high. Since impurities become a cause of a decrease in sensitivity characteristics of the scintillator, an amount thereof is preferably as small as possible. A phosphate radical ($PO_4$) of the impurities causes the decrease in sensitivity characteristics, and therefore its content is preferably 150 ppm or less. Further, in the case of using fluoride or the like as a sintering aid to achieve densification, the sintering aid remains as an impurity, thereby causing the decrease in sensitivity characteristics.

The sintered compact (polycrystal) of the rare earth oxysulfide phosphor has a structure composed of crystal grains in which a mean intercept length of the crystal grains measured on a scanning electron microscope (SEM) observation image is not less than 5.0 μm nor more than 30.0 μm. The above-described mean intercept length defines an average crystal grain diameter of the crystal grains. An example of the SEM observation image includes a SEM photograph obtained by SEM observation.

The above-described mean intercept length is measured as follows. A surface of the sintered compact is mirror-polished, and further etched by an etching solution prepared at a ratio of hydrochloric acid:hydrogen peroxide solution:water=1:1:1. After drying, an arbitrary surface is observed by the SEM. In a magnified image (SEM observation image) indicating an aggregation of crystal grains as a result of the SEM observation, arbitrary crystal grains are observed under magnification at high magnification such as 350 times or 700 times, and the magnified image (SEM observation image) in a unit area of 500 μm×500 μm is photographed, for example. By using this SEM observation image, an intercept length is measured by a line intercept method. In the line intercept method, an arbitrary straight line (corresponding to a length of 500 μm) is drawn on the observation image, and the number of crystal grains present on the line is counted, to obtain a mean intercept length on each line from an expression (500 μm/the number of crystal grains on the straight line of 500 μm). A mean value of intercept lengths measured by performing this work three times is set as the mean intercept length (μm). The average crystal grain diameter in the present specification indicates this mean intercept length.

With downsizing of the detection element, miniaturization of an element, and the like, it is necessary to cut the sintered compact of the above-described solid scintillator obtained by a sintering process to form a scintillator plate having such a size as, for example, 20 mm or more in width (short side), 30 mm or more in length (long side), and 0.5 mm or more in thickness, and form rectangular parallelepiped-shaped scintillator elements in each of which a longitudinal length of a surface corresponding to a surface on which X-rays are incident is 1 mm or less and a lateral length thereof is 1 mm or less (1 mm or less×1 mm or less in area (1 mm² or less)), and moreover, a longitudinal length thereof is 0.5 mm or less and a lateral length thereof is 0.5 mm or less (0.5 mm or less×0.5 mm or less in area (0.25 mm² or less)), from this scintillator plate. Then, in a scintillator array formed by integrating these fine scintillator elements, a width of the reflective layer is required to be narrower than 80 μm and to be 50 μm or less.

The sintered compact of the solid scintillator is a polycrystal. However, when a distribution of crystal grains is in a state in which coarse crystal grains (coarse grains) and minute crystal grains are mixed with one another, an average crystal grain diameter of crystal grains in the scintillator element and between the scintillator elements is not uniform, so that variations in characteristics of light output or the like of the above-described scintillator array are likely to increase. In particular, when the above-described scintillator element is downsized and miniaturized as a size of the above-described scintillator element has the longitudinal length of 1 mm or less and the lateral length of 1 mm or less, and moreover, the longitudinal length of 0.5 mm or less and the lateral length of 0.5 mm or less in the area of the surface corresponding to the surface on which X-rays are incident, in the case where a mixed region of coarse grains and minute crystal grains is present as is conventional, the mixed region becomes a cause of an increase in variations in emission characteristics.

In the scintillator array in which the above-described plurality of scintillator elements are arranged two-dimensionally in longitudinal and lateral directions with the reflective layers each interposed therebetween, a partial decrease in light output of the scintillator element causes a problem that sensitivity variations as the scintillator array increase. In the scintillator element, when the mixed region of coarse grains and minute crystal grains is present in a sintered ingot, light output of the individual scintillator elements is likely to decrease. This leads to the sensitivity variations in the scintillator array.

The presence of a defective portion in the inside of, on the surface of, and in the outer peripheral portion of the scintillator element formed by cutting the above-described sintered compact decreases light output when an X-ray is converted to visible light, similarly to the presence of the mixed region of crystal grains as described above. The above-described defective portion includes at least one selected from the group consisting of, for example, a hole, a flaw, a foreign material, and a hetero-phase. Examples of the hole include a pore and a void. Examples of the flaw include a crack, a fracture, peeling, chipping, and a chip. Examples of the foreign material include a substance having a component different from that of the rare earth oxysulfide phosphor. Examples of the hetero-phase include a region having the same components as those of, and a crystal structure different from that of, the above-described rare earth oxysulfide phosphor, and a region containing the impurity component in a large amount in the same components as those of the above-described rare earth oxysulfide phosphor.

In the above-described scintillator array in which a maximum length or a maximum diameter of defects present on the surface of the polycrystal is 40 μm or less, on the outer peripheral surface (surface) of the scintillator element formed by cutting the above-described solid scintillator or at least one of all edges including vertexes of the rectangular parallelepiped, a defect having a maximum length or a maximum diameter of not less than 0 μm nor more than 40 μm is likely to occur. When the maximum length of the defects exceeds 40 μm, characteristic values of light output or the like decrease due to these defects, so that variations in characteristics increase.

In the inside of the scintillator element, a total area ratio of the defective portion in a scanning surface subjected to ultrasonic flaw detection, namely, a ratio of a total area of the defective portion relative to an area of the scanning surface is preferably 10% or less. A measurement condition of the ultrasonic flaw detection is a frequency of 200 MHz, a focal length of 2.9 mm, a scanning pitch of 2.5 μm, a scanning surface size of 1 mm×1 mm, a sample thickness of 1 mm, and a detection limit defect length of 3 μm. When the above-described area ratio exceeds 10%, the characteristic values decrease due to these defects similarly to the above, so that the variations in characteristics are large. Note that when the sample thickness is less than 1 mm, the measurement is performed more than once until it becomes a thickness of 1 mm in total.

In the scintillator array, the defects present on the above-described outer peripheral surface or all edges including vertexes of the rectangular parallelepiped and the defects in the inside of the above-described scintillator element include at least one selected from the group constituted of, for example, a hole, a flaw, a foreign material, and a hetero-phase. The maximum length or the maximum diameter of the defects present on the surface of the polycrystal and the maximum length of the defects present on all the edges including at least one of vertexes of the polycrystal are more preferably each 40 μm or less.

Next, a manufacturing method example of the scintillator array of the embodiment will be explained. First, each of rare earth elements such as Gd and Pr is weighed in a predetermined amount, and these are sufficiently mixed with each other. As the respective starting materials, for example, the respective rare earth element oxides such as gadolinium oxide and praseodymium oxide are used. As a mixture of these respective starting materials, a uniform mixed oxide indicated below is preferably used. The uniform mixed oxide is formed by, for example, dissolving the respective rare earth element oxides in a nitric acid or the like, and thereafter coprecipitating them with an oxalic acid or the like, and burning a coprecipitate containing the respective rare earth elements at 900 to 1000° C.

Next, a mixed oxide powder of the above-described rare earth elements, for example, a $Gd_2O_3$ powder containing $Pr_2O_3$ of $5\times10^{-5}$ to $1\times10_{-2}$ mol, a sulphidizing agent such as a sulfur (S) powder, and flux such as $M_3PO_4$ or $M_2CO_3$ (M is at least one element selected from the group consisting of Li, Na, K, Rb, and Cs) are sufficiently mixed with one another. The mixed powder is burned at temperatures of 1100 to 1300° C. for five to ten hours, and thereafter washed by acid and water to form a rare earth oxysulfide phosphor powder.

The above-described rare earth oxysulfide phosphor powder is used as a material of phosphor ceramics composing the scintillator array of the embodiment. In the above-described rare earth oxysulfide phosphor powder to be used, a mean particle diameter is preferably not less than 0.05 μm nor more than 20 μm. When the mean particle diameter is less than 0.05 μm, a filling factor decreases in the manufacturing method to be described later, for example, at the stage of rubber press molding. For this reason, contraction is increased by sintering using a hot isostatic pressing (HIP) method in which high-temperature pressing is performed, and a failure is very likely to occur based on an increase in a contraction amount of a metal capsule. On the other hand, when the mean particle diameter of the rare earth oxysulfide phosphor powder exceeds 20 μm, a temperature is required to be made higher in HIP, so that strength, sensitivity, sensitivity distribution and so on of light output tend to decrease. The above-described mean particle diameter is further preferably not less than 0.05 μm nor more than 10 μm.

The sintered ingot of the solid scintillator is formed next. The sintered ingot of the solid scintillator is formed by a sintering method or the like using, for example, the HIP method, a hot press (HP) method, a spark plasma sintering (SPS) method, or a microwave heating method or a millimeter-wave heating method.

As HIP processing, when the above-described high-purity rare earth oxysulfide phosphor powder is molded in a suitable shape by a rubber press, and thereafter filled in a high melting point metal container composed of Ta, Mo, Nb, W and so on, or the like to be sealed, and sintered by performing the HIP processing under high-temperature and high-pressure conditions, crystal grains grow with progress of HIP sintering. Further, as another sintering method, a sintering method using the HP method, the SPS method, the microwave heating method, or the millimeter-wave heating method is also preferable.

In the HIP processing, together with progress of the HIP processing, from a sintered mass of primary particles of the above-described rare earth oxysulfide phosphor powder, for example, a structure (mixed structure) in which relatively small crystal grains each seen to be a long bar shape and relatively large crystal grains each having an irregular polygonal shape are mixed with one another is observed. Moreover, when the HIP processing progresses, the entire sintered compact grows into irregular polygonal crystal grains.

In order to obtain an optimal sintered compact, it is particularly important in this embodiment to control sintering conditions of the sintering method using, for example, the HIP method, the HP method, the SPS method, the microwave heating method, or the millimeter-wave heating method, or the like. In order to obtain a sintered compact being an optimal solid scintillator in this embodiment, in a manufacturing method of the sintered compact having each crystal grain structure of the above-described rare earth oxysulfide phosphor, in a case of having an irregular polygonal crystal grain structure having a uniform average crystal grain diameter, it is possible to obtain a solid scintillator excellent in sensitivity characteristics and uniformity of sensitivity of light output. That is, a sintered compact having no mixed structure exhibits light output characteristics to be optimal and reduce variations as a solid scintillator.

Such a growth process of the crystal grains of the rare earth oxysulfide phosphor, and light output sensitivity characteristics based thereon are found for the first time as a result of, regarding many samples produced by changing processing conditions of the sintering method using the HIP method, the HP method, the SPS method, the microwave heating method, or the millimeter-wave heating method, or the like, observing crystal grains appearing on their cross sections and measuring sensitivity and a sensitivity distribution of light output.

A HIP set temperature (thermal processing temperature) is preferably not lower than 1300° C. nor higher than 1500° C. When the HIP set temperature is lower than 1300° C., crystal growth cannot be sufficiently promoted. When the HIP set temperature exceeds 1500° C., the crystal growth progresses rapidly, and it becomes difficult to obtain a uniform crystal structure having a uniform crystal grain diameter. A more preferable HIP set temperature is not lower than 1340° C. nor higher than 1450° C.

A HIP pressure is preferably 98 MPa or more. When the HIP pressure is less than 98 MPa, an effect by the HIP processing cannot be sufficiently obtained. The HIP pressure is more preferably 118 MPa or more. When the HIP temperature is not lower than 1300° C. nor higher than 1500° C. and the HIP pressure is 98 MPa or more, a HIP time is preferably not shorter than 0.1 hours nor longer than 10 hours. A more preferable HIP time is not shorter than 0.25 hours nor longer than 8 hours. When the HIP time is shorter than 0.1 hours, crystal grains cannot be made to grow sufficiently, and when it exceeds 10 hours, too much growth of crystal grains makes coarse grains likely to be mixed.

Subjecting the rare earth oxysulfide phosphor powder to the HIP processing under such conditions makes it possible to adjust a sintered compact being a solid scintillator to a uniform crystal grain structure. That is, the scintillator array of the embodiment can be obtained with good reproducibility.

In the HP method, it is preferable to use a rare earth oxysulfide phosphor having a mean particle diameter of not less than 0.05 μm nor more than 0.5 μm as a raw material of the above-described sintered compact, and to perform sintering as the above-described processing conditions of HP at a time of manufacturing the above-described sintered compact, in which a sintering set temperature is not lower than 1350° C. nor higher than 1650° C., a sintering time is not shorter than 0.1 hours nor longer than 10 hours, and a processing pressure is 30 MPa or more, preferably 50 MPa or more. Using the above-described rare earth oxysulfide phosphor having minute particles whose mean particle diameter is not less than 0.05 μm nor more than 0.5 μm as the raw material causes a crystal grain structure of a sintered compact after sintering to have fine and uniform average crystal grain diameter, improves uniformity of characteristics of light output or the like to be affected by the crystal grain structure, and makes it possible to reduce variations. Moreover, since the raw material is minute particles, and adhesion strength of a grain boundary between powder particles is high, the defects such as the hole, the pore, the void, the flaw, the crack, the fracture, the peeling, the chipping, and the chip are unlikely to occur even though sudden strain relaxation force is generated in the inside of the sintered compact in the sintering process, and such defects as describe above are unlikely to occur even in plastic working such as machining in a post-process, so that variations in characteristic values due to a local decrease in light characteristics caused by the above-described defects and a decrease in operating life with progress of the above-described defects due to a change with passage of time at a time of use are suppressed.

Before performing main sintering by the HIP processing or the HP, it is preferable to perform a thermal processing process of holding at a temperature 50° to 300° C. lower than a main sintering temperature. Further, a holding time is preferably not shorter than 0.5 hours nor longer than 3 hours, for example.

Before performing the main sintering, holding at a predetermined temperature allows a temperature of the sample to be uniformalized. When a scintillator is sintered by the HIP processing, a capsule method is used. Using a capsule makes it possible to prevent mixing of a foreign material (impurity). The HIP processing is a method of sintering a sample put in the capsule while applying isotropic pressure thereto. By performing the HIP processing after uniformalizing the temperature of the sample in the capsule, grain growth can be homogenized. This allows a mean intercept length or a maximum diameter of intercept lengths to fall within a predetermined range.

When the scintillator is sintered by the HP, a metal mold press method can be used. The metal mold press method is a method of applying pressure in a uniaxial direction. The HP is a method of sintering while applying pressure in a uniaxial direction. For this reason, non-uniformity is likely to occur between a central portion and an outer peripheral portion of the sample. This is because the outer peripheral portion of the sample touches a metal mold. Sintering by the HP after homogenizing a temperature of the sample in the metal mold allows the grain growth to be homogenized. This allows the mean intercept length or the maximum diameter of the intercept lengths to fall within the predetermined range.

When the HIP processing and the HP are compared, a crystal grain diameter is more likely to become non-uniform in the HP by just as much as the metal mold is used. Therefore, in the thermal processing before the main sintering, the HP has a higher effect of improvement.

As another method example of forming the sintered compact being the solid scintillator, the sintering method by the SPS method, or microwave heating or millimeter-wave heating is preferable. In the sintering method by the SPS method, or the microwave heating or the millimeter-wave heating, pulverized powder particles self-heat to be sintered (pressure-sintered in the SPS method) at the portions where they are in direct contact with one another, so that it is possible to obtain a sintered compact having dense and uniform fine crystal grains, for a short time.

In the sintering method by the SPS method, or the microwave heating or the millimeter-wave heating, as described above, since the inside of the above-described pulverized powder particles is made to generate heat to be sintered by self-heating (while pressurizing in the SPS method), the sintering is possible under a not-so-high temperature condition for a short time, so that crystals remain fine to become a uniform crystal grain structure. The uniform crystal grain structure improves the uniformity of the characteristics of the light output or the like to be affected by the crystal grain structure, and makes it possible to reduce variations. Further, due to uniform and fine crystal grains, and since the original pulverized powder particles make the inside thereof generate heat to be sintered (pressure-sintered in the SPS method) at the places contact with one another by self-heating, and adhesion strength of a grain boundary between pulverized powder particles is also improved, the defects such as the hole, the pore, the void, the flaw, the crack, the fracture, the peeling, the chipping, and the chip are unlikely to occur even though the sudden strain relaxation force is generated in the inside of the sintered compact in the sintering process, and such defects as describe above are unlikely to occur even in the plastic working such as machining in the post-process, so that variations in characteristic values due to the local decrease in light characteristics caused by the above-described defects and a decrease in operating life with progress of the above-described defects due to a change with passage of time at a time of use are suppressed. Moreover, in the sintering method by the SPS method, or the microwave heating or the millimeter-wave heating, sintering in a near net shape close to a finished shape is possible, and a machining process such as a cutting process after sintering can be significantly omitted. Manufacturing in the near net shape makes it possible to suppress variations in characteristics of individual light outputs or the like of a plurality of the above-described solid scintillators.

A structure of the above-described sintered compact preferably has irregular polygonal crystal grains whose mean intercept length measured by using a SEM observation image is not less than 5.0 μm nor more than 30.0 μm. When the above-described mean intercept length is less than 5.0 μm or exceeds 30.0 μm, the strength and the sensitivity of light output are likely to decrease, the sensitivity distribution is also likely to become non-uniform. The intercept length is preferably 100 μm or less. Even though the mean intercept length falls within a range of not less than 5.0 μm nor more than 30.0 μm, a too large crystal grain diameter is likely to cause a non-uniform sensitivity distribution. Further the large crystal grain is likely to cause a defect when the grain is dropped in performing the machining.

As the above-describe processing conditions of the sintering method by the SPS method for obtaining the sintered compact of the solid scintillator being the crystal grains whose mean intercept length measured on the SEM observation image is not less than 5.0 μm nor more than 30.0 μm as an average crystal grain diameter of the crystal grains, it is preferable that a sintering reached temperature is 1400° C. or higher, and preferably not lower than 1400° C. nor higher than 1700° C., a sintering retention time is not shorter than 0.1 hours nor longer than 8 hours, and preferably 0.25 hours and 8 hours or shorter, and a reached pressurizing force at a time of molding is 50 MPa or more, and preferably 60 MPa or more. When the sintering reached temperature exceeds 1700° C., the crystal growth progresses rapidly, and it becomes difficult to obtain a uniform crystal structure having a uniform crystal grain diameter. When the sintering reached time is shorter than 0.1 hours, the crystal grains do not sufficiently grow, and when it exceeds 8 hours, too much growth of the crystal grains makes coarse grains likely to be mixed.

A mold to be used in the SPS method is preferably a mold made of carbon. The mold made of carbon makes it possible to obtain effects of oxidation prevention and impurity-mixing prevention of a molded body. Further, the process is preferably performed with pressure applied in a vacuum of $1 \times 10^{-3}$ Pa or less.

As the above-described processing conditions of the sintering method by the microwave heating or the millimeter-wave heating for obtaining the sintered compact of the solid scintillator constituting the scintillator array of the embodiment and being the crystal grains whose mean intercept length measured on the SEM observation image is not less than 5.0 μm nor more than 30.0 μm as an average crystal grain diameter of the crystal grains, it is preferable that a sintering reached temperature is 1300° C. or higher, and preferably not lower than 1300° C. nor higher than 1700° C., and a sintering retention time is not shorter than 0.1 hours nor longer than 8 hours, and preferably not shorter than 0.25 hours nor longer than 8 hours. When the sintering reached temperature is lower than 1300° C., the crystal growth cannot be sufficiently promoted. On the other hand, when the sintering reached temperature exceeds 1700° C., the crystal growth progresses rapidly, and it becomes difficult to obtain a uniform crystal grain structure having a uniform crystal grain diameter. When the sintering reached time is shorter than 0.1 hours, the crystal grains do not sufficiently grow, and when it exceeds 8 hours, too much growth of the crystal grains makes coarse grains likely to be mixed.

Since the sintered compact of the above-described solid scintillator constituting the scintillator array of the embodiment has a crystal grain structure having a uniform crystal grain diameter and is excellent in uniformity of characteristics, even the sintered compact of the above-described solid scintillator having a large size can be stably obtained, and moreover, the characteristics can be kept good, and it also becomes possible to significantly reduce the variations in characteristics.

By processing the sintered compact of the above-described solid scintillator, a rectangular bar-shaped scintillator plate can be formed. The scintillator plate is processed into scintillator elements, and is used for an X-ray detector or the like as a scintillator array obtained by integrating them with a plurality of reflective layers each interposed therebetween. The scintillator array has a shape having, for example, 20 mm or more in length in a short-side direction, 30 mm or more in length in a long-side direction, and 0.5 mm or more in thickness.

The reflective layer for integrating the above-described plurality of scintillator elements is preferably composed of, for example, a mixture of reflector particles of titanium oxide, aluminum oxide, or the like and transparent resin in order to make it difficult to leak light emitted from the scintillator elements by radiation rays such as X-rays to the neighboring scintillator elements. As the reflective layer, other than the above, a white polyethylene terephthalate (PET) film, a metal deposited film, or the like may be used.

The above-described scintillator plate is processed (cut) into the scintillator elements each having a predetermined geometry by the machining including the cutting process with a wire saw, a dicer, or the like. It is preferable to process the scintillator plate by the machining which does not apply a stress equal to or more than a yield stress of the above-described sintered compact to the above-described sintered compact as the above-described processing conditions. For that purpose, a blade edge of the dicer to process the scintillator plate into a predetermined scintillator element shape, or the like is set as a cutting blade unlikely to cause the defects such as the fracture, the crack, the chipping, the flaw, the chip, and the peeling, to make a blade thickness thereof thin or to use, for a material of the blade, the one made of cemented carbide or cermet, thereby making it possible to suppress occurrence of the above-described defects due to the process.

It is preferable to perform the cutting process by using the cutting blade whose thickness of the blade is 100 μm or less. When the thickness of the blade exceeds 100 μm, the stress equal to or more than the yield stress of the sintered compact is likely to be applied to the sintered compact at a time of the cutting process, and the above-described defects are likely to occur. The blade thickness of the cutting blade is more preferably 60 μm or less.

When the above-described sintered compact is machined, by performing the cutting process by ultrasonic-vibrating the cutting blade in a radial direction of the sintered compact at a time of driving the dicer as the above-described processing conditions, it is possible to easily remove a cutting powder and reduce clogging, and reduce grazing of the cutting blade, so that it is possible to reduce a load at a time of the process and suppress the occurrence of the defects due to the process.

As a method for avoiding the application of the stress equal to or more than the yield stress of the sintered compact to the sintered compact (scintillator) at a time of the cutting process, it is cited to use a material having high hardness for the cutting blade or to make the thickness of the cutting blade thin. Further, it is cited to increase a rotational speed of the cutting blade, to decrease a feed speed of the cutting blade, to control a one-time cutting depth, or the like. These may be combined with one another.

The rotational speed of the cutting blade is preferably not less than 5000 rpm nor more than 20000 rpm. The rotational speed is slow at less than 5000 rpm, so that the stress is likely to be high. Further, when it exceeds 20000 rpm, the thin cutting blade sways to cause the stress to be easily applied. For this reason, the rotational speed of the cutting blade is preferably not less than 5000 rpm nor more than 20000 rpm, and further not less than 7000 rpm nor more than 15000 rpm.

The feed speed of the cutting blade is preferably 6 mm/s or less. The feed speed of the cutting blade is a speed which puts forward the cutting blade in a fixed direction. Decreasing the feed speed makes it possible to reduce the stress to be applied to the sintered compact (scintillator) at a time of the cutting process. For this reason, the feed speed of the cutting blade is preferably 6 mm/s or less, and further 5 mm/s or less.

A thickness T1 of the sintered compact (scintillator) and a one-time cutting depth T2 preferably satisfy $0.25 \leq (T2/T1) \leq 0.95$. $T2/T1=1$ indicates that the one-time cutting depth is the same as the thickness of the sintered compact. T2/T1 being not less than 0.25 nor more than 0.95 indicates that the thickness T1 of the sintered compact is cut by dividing the cutting process into plural times. Reducing the one-time cutting depth allows the stress to be reduced. Note that T2/T1 may be less than 0.25, but increasing the number of times of the process causes a long lead time.

Since the sintered compact of the above-described solid scintillator constituting the scintillator array of the embodiment is excellent in light output sensitivity characteristics, and further excellent in uniformity of the sensitivity distribution, using the scintillator element processed as described above as a fluorescence generator of an X-ray detector makes it possible to achieve downsizing of a detection element, an improvement in detection sensitivity of X-rays, suppression of an artifact, and the like. This greatly contributes to downsizing•high resolution of the X-ray detector, or the like.

The above-described scintillator plate is required to be made longer in order to cope with an increase in the number of segments (the number of scintillator elements) per one channel of the X-ray detector, or the like. Using the sintered compact of the above-described solid scintillator constituting the scintillator array of the embodiment makes it possible to achieve a scintillator plate having a length of 30 mm or more, for example. Moreover, even a long-sized scintillator plate having a length of 90 mm or more, and further 300 mm or more can be put to practical use. Such a scintillator plate to which the sintered compact of the above-described solid scintillator constituting the scintillator array of the embodiment is applied is a crystal grain structure having a uniform crystal grain diameter as described above, so that the uniformity of characteristics can be stably obtained.

By the above-described long-sized scintillator plate, one channel can be constituted of a plurality of segments (scintillator elements) cut out of one plate. That is, it becomes possible to uniformalize characteristics of each of channels of the X-ray detector. For example, in a multi-tomogram type X-ray CT scanner, one channel is constituted of many segments (scintillator elements). The scintillator plate composed of the sintered compact of the above-described solid scintillator constituting the scintillator array of the embodiment is suitable for such a use.

A radiation detector of the embodiment includes the scintillator array, and includes: a fluorescence generator which emits fluorescence in response to radiation rays incident on the scintillator array; and a photoelectric converter which receives light from the fluorescence generator and converts the light into electricity.

The above-described fluorescence generator has the scintillator array constituted by integrating a plurality of scintillator elements each formed by slicing or grooving-processing the scintillator plate composed of the sintered compact of the above-described solid scintillator in longitudinal and lateral directions with the reflective layers each interposed therebetween. The above-described fluorescence generator may include a plurality of channels, and each of the above-described plurality of channels may have a constitution in which a plurality of segments (scintillator elements) produced by slicing the above-described scintillator plate are integrated in a direction substantially orthogonal to an array direction of each of the above-described plurality of channels with the reflective layers each interposed therebetween.

A radiation inspection device of the embodiment may include: a radiation source which irradiates an inspection object with radiation rays; and the radiation detector which detects radiation rays which the inspection object transmits. The radiation inspection device may be an X-ray tomograph.

Figure 3:
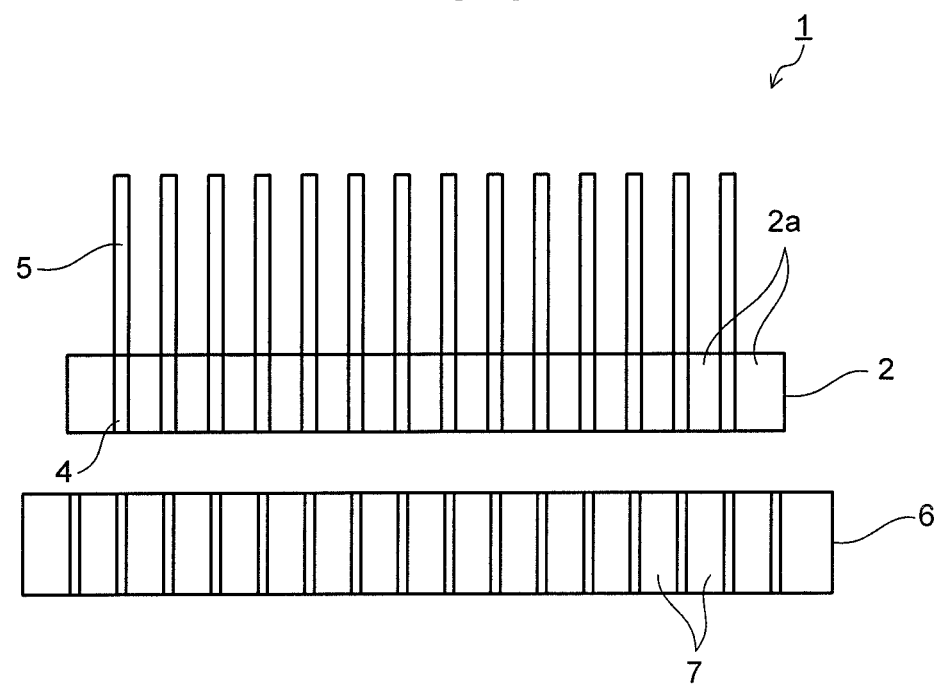
FIG. 3 is a view illustrating a constitution example of an X-ray detector.
Figure 4:
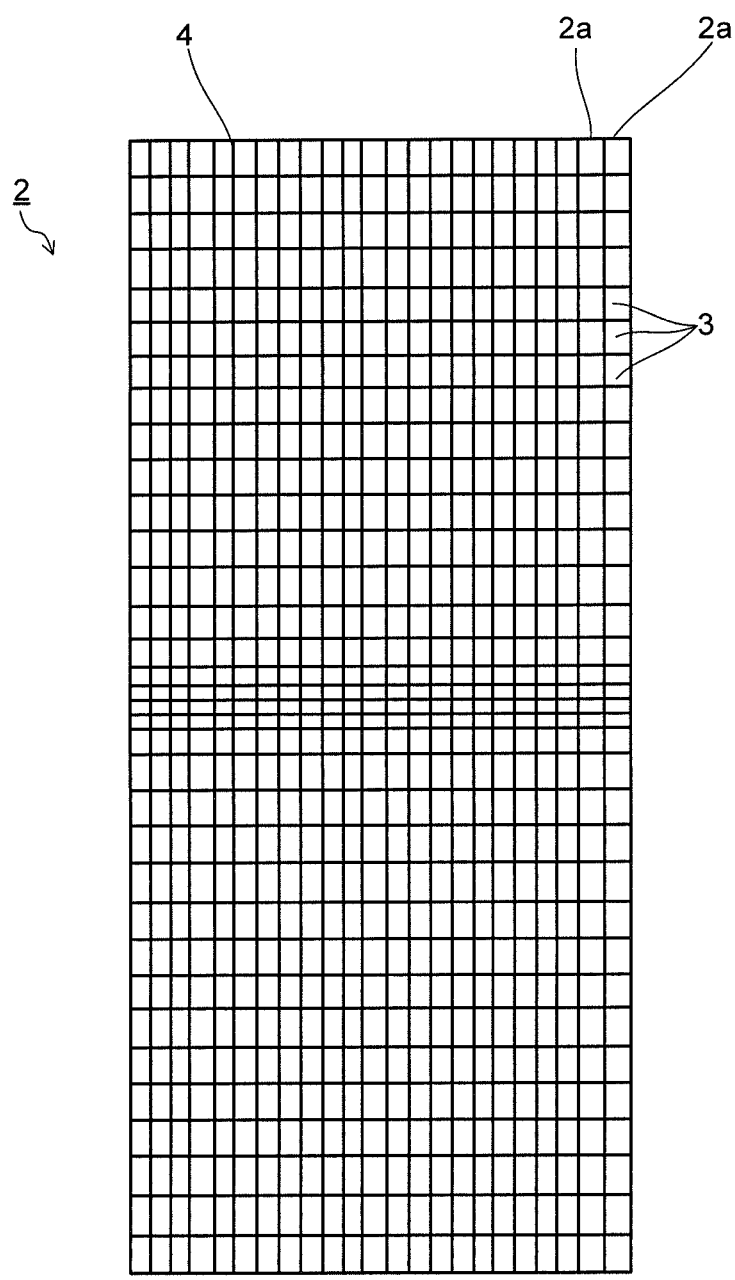
FIG. 4 is a view illustrating a constitution example of a scintillator array.

Next, constitution examples of the radiation detector and the radiation inspection device will be explained with reference to FIG. 3, FIG. 4, and FIG. 5. FIG. 3 is a view illustrating a constitution example of an X-ray detector. An X-ray detector 1 illustrated in FIG. 3 has a scintillator array 2 as a fluorescence generator (fluorescence source). FIG. 4 is a view illustrating a constitution example of the scintillator array 2. The scintillator array 2 is constituted by integrating a plurality of segments (scintillator elements) 3 cut out of the scintillator plate described above in longitudinal and lateral directions with the reflective layers each interposed therebetween.

In the scintillator array 2, for each of channels 2a, the plurality of segments (scintillator elements) 3 cut out of one scintillator plate are used, for example. Then, by lining up the plurality of segments (scintillator elements) 3 each formed by cutting this one scintillator plate in a column direction, the respective channels 2a are constituted. In the scintillator array 2, reflective layers 4 are each interposed between the channels 2a. The scintillator plate may be grooving-processed to form an array including channels and segments in a grid shape from the one plate. The reflective layers 4 are interposed between the respective channels and the respective segments.

In front of the respective channels 2a of the scintillator array 2, collimators 5 which regulate an incident direction of X-rays are provided, block X-rays incident from an oblique direction, and lead only perpendicularly incident X-rays into the scintillator array 2. The collimators 5 are each disposed so as to regulate the incident direction of X-rays for each of the channels 2a. In rearward of the scintillator array 2, a photoelectric conversion part 6 is provided. The photoelectric conversion part 6 has a plurality of photodiodes 7 disposed to correspond to the respective segments 3 of the scintillator array 2.

In the above-described X-ray detector 1, X-rays are incident on the scintillator array 2, and the respective segments 3 of the scintillator array 2 emit light according to this incident X-ray dosage. The light emitted from each of the segments 3 is detected by each of the photodiodes 7. That is, an output of the light emitted based on the incident X-ray dosage is converted to an electrical output by the photodiodes 7, thereby measuring an incident X-ray dosage.

Since the channels 2a of the scintillator array 2 are each constituted of the plurality of segments 3 each formed by cutting the scintillator plate, the X-ray detector 1 can improve detection sensitivity of X-rays, and enhance uniformity of sensitivity (output) for each of the channels 2a. These allow a significant improvement in characteristics and accuracy of the X-ray detector 1. The X-ray detector 1 is suitably used for the multi-tomogram type X-ray CT scanner. The X-ray detector 1 is fabricated with good accuracy and a high yield.

Figure 5:
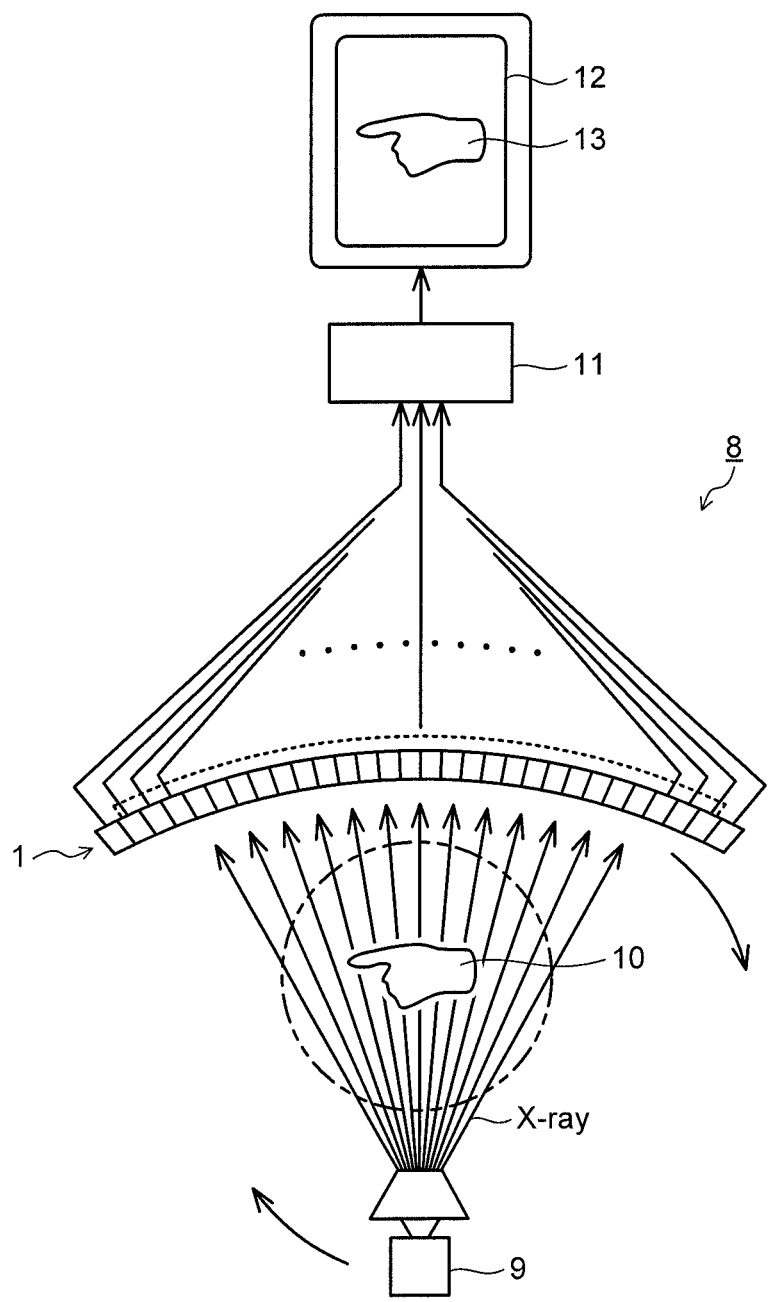
FIG. 5 is a view illustrating a constitution example of an X-ray inspection device.

FIG. 5 is a view illustrating a constitution example of an X-ray inspection device. An X-ray CT scanner 8 illustrated in FIG. 5 includes the X-ray detector 1. The X-ray detector 1 is attached on an inner wall of a cylinder in which an imaging region of a subject 10 is laid to rest. Substantially at the center of a circular arc on which the X-ray detector 1 has been attached, an X-ray tube 9 which radiates X-rays is disposed. Between the X-ray detector 1 and the X-ray tube 9, the fixed subject 10 is disposed. The X-ray detector 1 and the X-ray tube 9 rotate while taking photographs by using X-rays with the fixed subject 10 centered. Thus, image information of the subject 10 is collected in three dimensions from different angles.

A signal obtained by X-ray photography is processed in a computer 11, and indicated as a subject image 13 on a display 12. The subject image 13 is, for example, a tomogram of the subject 10. In the multi-tomogram type X-ray CT scanner, a plurality of tomograms of the subject 10 are simultaneously photographed. According to such a multi-tomogram type X-ray CT scanner, photographed results can also be depicted in three dimensions.

The X-ray CT scanner 8 as described above can effectively prevent appearance of an artifact (quasi-image), or the like since the scintillator plate excellent in uniformity of the sensitivity distribution is used even in a case of the long-sized one. Moreover, a high output from each scintillator allows an improvement in resolution, or the like to be achieved. These make it possible to significantly enhance medical diagnosis performance based on the X-ray CT scanner 8.

Note that the radiation inspection device is applicable not only to an X-ray inspection device for medical diagnosis but also to an industrial-use X-ray nondestructive inspection device, or the like. This embodiment also contributes to an improvement in inspection accuracy by using the X-ray nondestructive inspection device, or the like.

EXAMPLES

Next, concrete examples of the embodiment and their evaluation results will be described.

Examples 1 to 13, Comparative Examples 1 to 6

A rare earth oxysulfide phosphor powder was molded by a rubber press, and this molded body was produced into a sintered compact by a sintering method by a HIP method, a HP method, or a SPS method under conditions presented in Table 1.

In a case of the HIP method, a molded body of a $Gd_2O_2S:Pr$ (Pr concentration=0.05 mol %) rare earth oxysulfide phosphor powder having a mean particle diameter of 6 μm was enclosed by deaeration in a capsule made of Ta, thereafter setting this in a HIP processing apparatus, and an argon gas was sealed as a pressurizing medium in the HIP processing apparatus, and processing was carried out under the respective processing conditions (pressure, temperature, time) presented in Table 1. In a case of the HP method, a mold made of carbon was filled with a $Gd_2O_2S:Pr$ (Pr concentration=0.05 mol %) phosphor powder having a mean particle diameter of 0.1 μm, and main sintering was performed under the respective conditions (temperature, time, pressure) presented in Table 1 while being pressurized.

In the HIP method and the HP method, thermal processing at a temperature 50° C. to 300° C. lower than a main sintering temperature was performed before the main sintering. The thermal processing conditions (temperature, time) before the main sintering are also presented in Table 1. Any thermal processing before the main sintering was performed at normal pressure.

In a case of the SPS method, a mold made of carbon was filled with the above-described temporarily molded body, and sintering (a spark plasma sintering method) was performed under the respective processing conditions (temperature, time, pressure) presented in Table 1 by passing and discharging a large current on-off DC pulse current while being pressurized in a vacuum of $1×10^{-4}$ Pa or less. Further, the thermal processing before the main sintering was not performed regarding any of comparative examples.

TABLE 1

| | Thermal processing before main sintering | | Main sintering | | | |
|---|---|---|---|---|---|---|
| | Temperature (° C.) | Time (h) | Sintering method | Temperature (° C.) | Time (h) | Pressure (MPa) |
| Example 1 | 1300 | 1 | HIP | 1375 | 3 | 147 |
| Example 2 | 1250 | 2 | HIP | 1375 | 6 | 147 |
| Example 3 | 1200 | 2.5 | HIP | 1375 | 9 | 147 |
| Example 4 | 1270 | 1 | HIP | 1325 | 3 | 147 |
| Example 5 | 1350 | 0.5 | HIP | 1425 | 3 | 147 |
| Example 6 | 1050 | 3 | HIP | 1375 | 3 | 98 |
| Example 7 | 1150 | 2 | HIP | 1375 | 3 | 118 |
| Example 8 | — | — | SPS | 1600 | 0.5 | 60 |
| Example 9 | — | — | SPS | 1500 | 1 | 80 |
| Example 10 | — | — | SPS | 1400 | 2 | 100 |
| Example 11 | 1250 | 2 | HP | 1350 | 5 | 50 |
| Example 12 | 1300 | 1 | HP | 1450 | 0.5 | 45 |
| Example 13 | 1350 | 1 | HP | 1550 | 1 | 40 |
| Comparative example 1 | — | — | HIP | 1290 | 12 | 147 |
| Comparative example 2 | — | — | HIP | 1470 | 0.05 | 147 |
| Comparative example 3 | — | — | HIP | 1375 | 3 | 80 |
| Comparative example 4 | — | — | SPS | 1300 | 0.5 | 180 |
| Comparative example 5 | — | — | SPS | 1380 | 0.5 | 40 |
| Comparative example 6 | — | — | HP | 1700 | 10 | 25 |

Thus, column-shaped sintered compacts (solid scintillators) each composed of rare earth oxysulfide phosphor and each having about 80 mm in diameter×about 120 mm in height were produced. The later-described characteristic evaluation was served with the above sintered compacts.

Each of the sintered compacts according to the above-described Examples 1 to 13 and Comparative examples 1 to 6 was cut to form a rectangular plate-shaped scintillator plate of 1 mm×80 mm×30 mm first, and moreover, the scintillator plate was cut to form rectangular parallelepiped chips of scintillator elements each having 0.5 mm×0.5 mm×1 mm. Conditions of cutting process are as presented in Table 2. A cutting blade at a time of a cut out process was set as cemented carbide. Further, a thickness of the cutting blade, a rotational speed, a feed speed, and a one-time cutting depth (T2/T1) are as presented in Table 2. Further, the one-time cutting depth (T2/T1) in the examples was set to 0.95 or less. The cutting process was performed by repeating the cut out process plural times. Further, a one-time cutting depth was set to T2/T1=1 to perform cut-out in a one-time process in the comparative examples.

TABLE 2

| | Cutting blade thickness (μm) | Rotational speed (rpm) | Feed speed (mm/s) | Cutting depth (T2/T1) |
|---|---|---|---|---|
| Example 1 | 40 | 8000 | 5 | 0.4 |
| Example 2 | 50 | 13000 | 5 | 0.5 |
| Example 3 | 40 | 17000 | 4 | 0.6 |
| Example 4 | 50 | 10000 | 4 | 0.5 |
| Example 5 | 50 | 12000 | 4 | 0.5 |
| Example 6 | 60 | 5000 | 6 | 0.9 |
| Example 7 | 40 | 8000 | 4 | 0.85 |
| Example 8 | 30 | 10000 | 3 | 0.7 |
| Example 9 | 50 | 12000 | 4 | 0.7 |
| Example 10 | 50 | 10000 | 4 | 0.85 |
| Example 11 | 50 | 10000 | 4 | 0.75 |
| Example 12 | 50 | 9000 | 3 | 0.75 |
| Example 13 | 30 | 9000 | 3 | 0.75 |
| Comparative example 1 | 70 | 8000 | 6 | 1 |
| Comparative example 2 | 70 | 8000 | 7 | 1 |
| Comparative example 3 | 70 | 8000 | 7 | 1 |
| Comparative example 4 | 70 | 8000 | 7 | 1 |
| Comparative example 5 | 70 | 8000 | 7 | 1 |
| Comparative example 6 | 70 | 3000 | 10 | 1 |

Scintillator arrays each having about 20 mm×about 40 mm×about 1 mm were each fabricated by integrating these rectangular parallelepiped chips with reflective layers (layer composed by mixing titanium oxide and resin) each having a width of 50 μm each interposed therebetween. The obtained scintillator arrays were each used to evaluate characteristics as follows.

Figure 2:
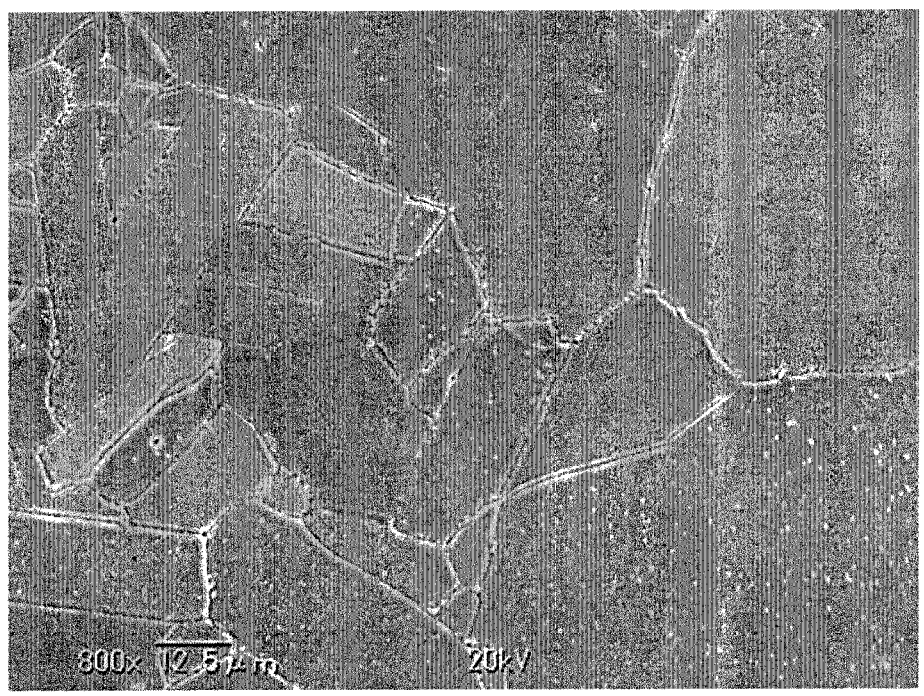
FIG. 2 is a view illustrating a crystal grain structure of a sintered compact of a solid scintillator.

A cut surface of each of the rectangular parallelepiped chips of the scintillator elements was lightly etched by an inorganic acid or the like, and a surface thereof was observed by a SEM. FIG. 1 is, of Example 1, and FIG. 2 is, of Comparative example 1, a magnified SEM observation image example of the cut surface of each of the rectangular parallelepiped chips of the scintillator elements. A distribution of a mean intercept length was obtained as an average crystal grain diameter of crystal grains on the SEM observation image. A specific measuring method of the mean intercept length measured on the SEM observation image as the average crystal grain diameter of crystal grains is as described above. Table 3 presents these results.

Internal defects of the above-described solid scintillator were measured as a total area ratio of the defective portion in a scanning surface subjected to ultrasonic flaw detection (conditions: a frequency of 200 MHz, a focal length of 2.9 mm, a scanning pitch of 2.5 μm, a scanning surface size of 1 mm×1 mm, a sample thickness of 2 mm, and a detection limit defect length of 3 μm) in a thickness direction regarding a surface parallel to an X-ray incident surface of the solid scintillator. In appearance defects, a maximum length or a maximum diameter of defects on an outer peripheral surface of the above-described scintillator element and a maximum defect length of defects present on the whole circumference of edges (including vertexes) of the rectangular parallelepiped chip (0.5 mm×0.5 mm×1 mm in size) of the above-described scintillator element were measured. Table 3 presents the area ratio of the internal defects and the maximum defect length of the appearance defects of the solid scintillator of each of the examples and the comparative examples.

Next, a ratio of a current flowing through silicon photodiodes installed at the rear by irradiating a surface of about 20 mm×about 40 mm of each of the scintillator arrays with X-rays (120 kV) to when a current value in Comparative example 3 was set to 100% was measured as sensitivity (light output) of each of the scintillator arrays. Sensitivity variations were obtained from, by irradiation with X-rays in order from an end of the scintillator array at a slit width of 1 mm with irradiation positions varied, variations in sensitivity of the respective portions, instead of irradiation of the whole surface with X-rays. Light outputs of the respective portions were obtained as percentages relative to that in Comparative example 3, and the above-described variations in sensitivity were obtained as a difference between a maximum value and a minimum value of the above respective output percentages. The one larger than 100% in the above-described sensitivity has more excellent light output (sensitivity characteristics). The smaller the above-described variations in sensitivity are, the more the variations are reduced. As the above-described comparison standard sample, a sample having the same dimensions was used after cutting out of the scintillator plate in which a distribution of crystal grains of Comparative example 1 was in a state in which minute crystal grains surrounded coarse columnar crystals. Table 3 presents these results.

TABLE 3

| | Crystal structure | | Defect | | Characteristic | |
|---|---|---|---|---|---|---|
| | Mean intercept length (μm) | Maximum value of intercept length (μm) | Internal defect area ratio (%) | Maximum appearance defect length (μm) | Sensitivity | Sensitivity variations |
| Example 1 | 8.8 | 26.5 | 3 | 12 | 179% | 2.8% |
| Example 2 | 11.5 | 30.1 | 5 | 14 | 189% | 2.9% |
| Example 3 | 14.1 | 32.6 | 6 | 16 | 196% | 4.2% |
| Example 4 | 5.6 | 22.6 | 2 | 14 | 201% | 3.0% |
| Example 5 | 28.4 | 84.8 | 3 | 15 | 202% | 4.4% |
| Example 6 | 9.4 | 28.4 | 7 | 20 | 199% | 2.9% |
| Example 7 | 9.2 | 37.1 | 3 | 19 | 201% | 4.2% |
| Example 8 | 7.5 | 35.8 | 2 | 16 | 198% | 4.2% |
| Example 9 | 6.6 | 33.9 | 4 | 17 | 200% | 3.0% |
| Example 10 | 5.4 | 16.2 | 5 | 21 | 195% | 4.7% |
| Example 11 | 12.6 | 28.8 | 4 | 19 | 200% | 2.5% |
| Example 12 | 24.1 | 75.4 | 5 | 18 | 199% | 3.1% |
| Example 13 | 19.7 | 45.5 | 3 | 16 | 201% | 2.4% |
| Comparative example 1 | 4.2 | 28.1 | 32 | 41 | 91% | 10.2% |
| Comparative example 2 | 42.5 | 230.1 | 27 | 55 | 92% | 9.1% |
| Comparative example 3 | 8.7 | 42 | 16 | 49 | 100% | 8.2% |
| Comparative example 4 | 3.6 | 27.5 | 31 | 46 | 93% | 9.3% |
| Comparative example 5 | 4.7 | 31.7 | 34 | 51 | 94% | 8.7% |
| Comparative example 6 | 61.3 | 303.7 | 38 | 63 | 89% | 9.2% |

As presented in Table 3, any scintillator array constituted of the solid scintillator of each of the examples has a crystal grain structure having a uniform irregular polygonal crystal grain diameter as clearly illustrated as an example in FIG. 1. Then, the scintillator array constituted of the solid scintillator sintered compact having such a crystal structure is found excellent in sensitivity characteristics and sensitivity variations as compared with the comparative examples.

As described above, the scintillator array of the embodiment makes it possible, for example, to obtain light output capable of coping with downsizing of the detector and the like, and further to achieve the sensitivity distribution in which variations are small and the light output is uniform, in addition to excellent light output (sensitivity characteristics). According to the radiation detector and the radiation inspection device of the embodiment using such a scintillator array, it becomes possible to increase resolution, image accuracy, and the like.

While certain embodiments of the present invention have been exemplified, these embodiments have been presented by way of example only, and are not intended to limit the scope of the inventions. Indeed, the novel embodiments described herein may be embodied in a variety of other forms; furthermore, various omissions, substitutions, changes and the like in the form of the embodiments described herein may be made without departing from the spirit of the inventions. The accompanying claims and their equivalents are intended to cover such forms or their modification examples as would fall within the scope and spirit of the inventions. Further the aforementioned embodiments may be embodied in combination with each other.

The invention claimed is:

1. A scintillator array comprising:
   a first scintillator element;
   a second scintillator element; and
   a reflector provided between the first and second scintillator elements and having a width of 80 μm or less therebetween,
   wherein each scintillator element includes a polycrystal containing a rare earth oxysulfide phosphor, the polycrystal having a radiation incident surface of 1 mm or less×1 mm or less in area,
   wherein an average crystal grain diameter of the polycrystal is not less than 5 μm nor more than 30 μm, the average crystal grain diameter being defined by an average intercept length of crystal grains in an observation image of the polycrystal with a scanning electron microscope,
   wherein a maximum length or a maximum diameter of defects on the polycrystal is 40 μm or less, and
   wherein a ratio of a total area of defects on a scanning surface to an area thereof is 10% or less, the ratio being defined by inspecting an inside of the polycrystal under a measurement condition including a frequency of 200

MHz, a focal length of 2.9 mm, a scanning pitch of 2.5 µm, a scanning surface size of 1 mm×1 mm, a sample thickness of 1 mm, and a detection limit defect length of 3 µm using ultrasonic flaw detection.

2. The scintillator array according to claim 1, wherein the defect includes at least one selected from the group consisting of a hole, a flaw, a foreign material including a component different from a component of the rare earth oxysulfide phosphor, a hetero-phase having the same components as components of, and a crystal structure different from a crystal structure of, the rare earth oxysulfide phosphor, and a hetero-phase including a component different from a component of the rare earth oxysulfide phosphor.

3. The scintillator array according to claim 1, wherein the rare earth oxysulfide phosphor is expressed by a formula of $A_2O_2S{:}Pr$, wherein A is at least one element selected from the group consisting of Y, Gd, La and Lu, or wherein the rare earth oxysulfide phosphor is expressed by a formula of $(Gd_{1-x}A'_x)_2O_2S{:}Pr$, wherein A' is at least one element selected from the group consisting of Y, La and Lu, and x is a number satisfying $0 \leq x \leq 0.1$.

4. The scintillator array according to claim 3, wherein the rare earth oxysulfide phosphor contains at least one element selected from the group consisting of cerium, zirconium, and phosphorus.

5. A radiation detector comprising:

the scintillator array according to claim 1; and a photoelectric converter to convert light from the scintillator array into electricity.

6. A radiation inspection device comprising:

a radiation source to irradiate an inspection object with radiation rays; and the radiation detector according to claim 5, the radiation detector being configured to detect radiation rays through the inspection object.

\* \* \* \* \*